United States Patent [19]
Monteiro et al.

[11] Patent Number: 5,855,721
[45] Date of Patent: Jan. 5, 1999

[54] NON-DESTRUCTIVE METHOD OF DETERMINING THE POSITION AND CONDITION OF REINFORCING STEEL IN CONCRETE

[75] Inventors: Paulo J. M. Monteiro; H. F. Morrison, both of Berkeley, Calif.

[73] Assignee: The Regents of the University of California, Oakland, Calif.

[21] Appl. No.: 814,912

[22] Filed: Mar. 12, 1997

[51] Int. Cl.[6] .................................................. B32B 31/00
[52] U.S. Cl. ................................. 156/274.4; 156/272.2; 73/658; 324/240; 324/536; 324/554; 324/700
[58] Field of Search ......................... 324/207.14, 207.17, 324/207.11, 326, 67, 236–238, 239–243, 207.22, 557, 558, 536, 559, 700, 235, 240, 207.26, 33; 73/649, 658; 340/660, 661; 156/274.4, 272.2, 378

[56] References Cited

U.S. PATENT DOCUMENTS

| | | | |
|---|---|---|---|
| 3,849,722 | 11/1974 | Nilsson | 324/9 |
| 4,139,814 | 2/1979 | Radd et al. | 324/33 |
| 4,531,091 | 7/1985 | Kusenberger et al. | 324/242 |
| 4,681,489 | 7/1987 | Millauer et al. | 408/1 R |
| 4,958,130 | 9/1990 | Mochizuki et al. | 324/700 |
| 5,084,680 | 1/1992 | Mitchell et al. | 324/559 |
| 5,098,543 | 3/1992 | Bennett et al. | 204/196 |
| 5,446,379 | 8/1995 | Machi | 324/240 |

FOREIGN PATENT DOCUMENTS

| | | |
|---|---|---|
| P03181 | of 1914 | United Kingdom . |
| 2132357 | 7/1984 | United Kingdom . |
| WO8809498A | 12/1988 | WIPO . |

OTHER PUBLICATIONS

Berke et al., "Comparison of the Polarization Resistance Technique to the Macrocell Corrosion Technique", *Corrosion Rates of Steel in Concrete*, ASTM, STP 1065, N.S. Berke et al., Eds., American Society for Testing and Materials, Philadelphia, 1990, pp. 38–43, 46–50.

Andrade, C., et al., "The Determination of the Corrosion Rate of Steel Embedded in Concrete by the Polarization Resistance and AC Impedance Methods", *Corrosion Effect of Stray Currents and the Techniques for Evaluating Corrosion of Rebars in Concrete*, ASTM STP 906, V. Chakar, Ed., American Society for Testing and Materials, Philadelphia, 1986, pp. 43–63.

Stratfull, Richard F., "Halfcell Potentials and The Corrosion of Steel in Concrete", *Highway Research Report, Interim Report*, State of California Business and Transportation Agency Department of Public Works Division of Highways, in Cooperation with the U.S. Dept. of Transportation, Federal Highway Administration, Nov. 1972.

Berke, N., et al., "Comparison of Current Interruption and Electrochemical Impedance Techniques in the Determination of Corrosion Rates of Steel in Concrete", *The Measurement and Correction of Electrolyte Resistance in Electrochemical Tests*, ASTM STP 1056, L.L. Scribner et al., Eds. American Society for Testing and Materials, Philadelphia, 1990, pp. 191–201.

Gonzalez, J.A. et al., "Errors in the Electrochemical Evaluation of Very Small Corrosion Rates–II. Other Electrochemical Techniques Applied to Corrosion of Steel in Concrete." *Corrosion Science*, vol. 25, No. 7, pp. 519–530, 1985.

(List continued on next page.)

Primary Examiner—Merrick Dixon
Attorney, Agent, or Firm—Flehr Hohbach Test Albritton & Herbert LLP

[57] ABSTRACT

A method of determining the position and condition of reinforcing steel embedded in concrete is described. The method is non-invasive. Electrodes are use to carry out the method by contacting the outer surface of the concrete. The method measures the impedance of selected regions of the concrete by measuring the voltage generated across said selected regions by a current flowing through the concrete.

10 Claims, 6 Drawing Sheets

OTHER PUBLICATIONS

Gonzalez, J.A. et al., "Errors in the Electrochemical Evaluation of Very Small Corrosion Rates–I. Polarization Resistance Method Applied to Corrosion of Steel in Concrete." *Corrosion Science*, vol. 25, No. 10, pp. 917–930, 1985.

Escalante, E. et al., "Measuring the Corrosion Rate of Reinforcing Steel in Concrete", *U.S. Department of Commerce National Bureau of Standards*, Apr. 1984.

Hladky, K. et al., "The Measurement of Corrosion Using Electrochemical 1/f Noise", *Corrosion Science*, 1982 vol. 22, No. 3, pp. 231–237.

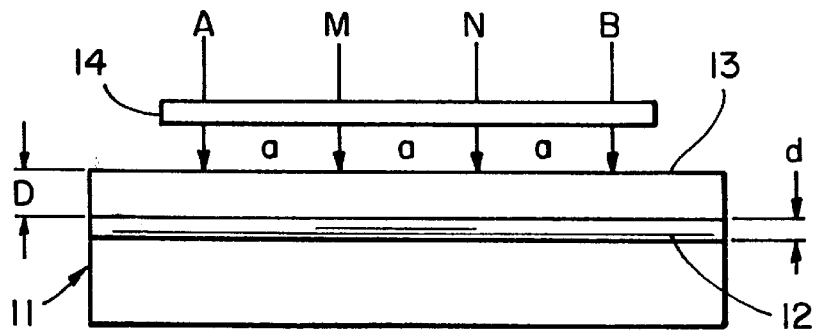
*FIG_1*
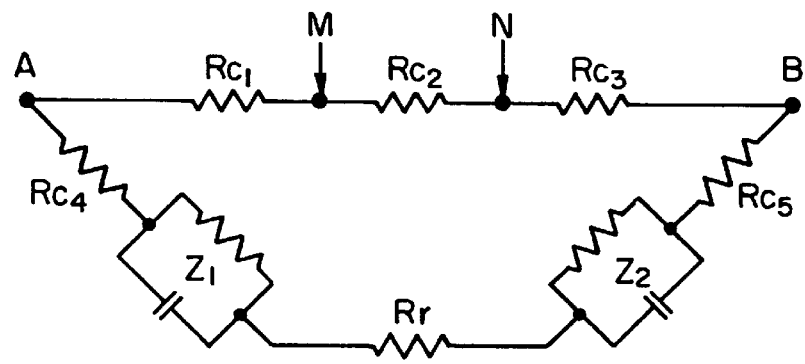
*FIG_2*
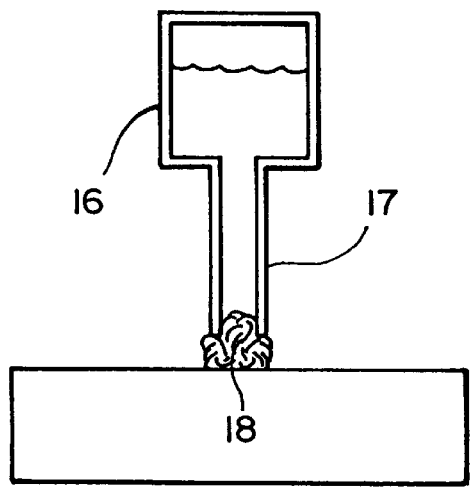
*FIG_3*

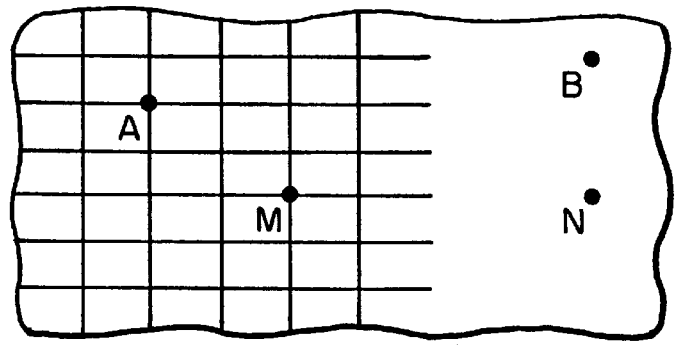
FIG_4
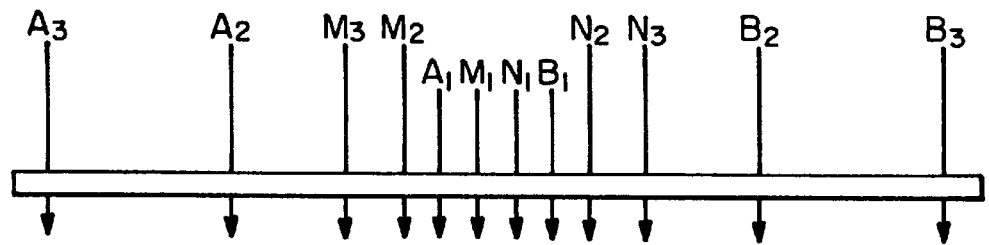
FIG_5
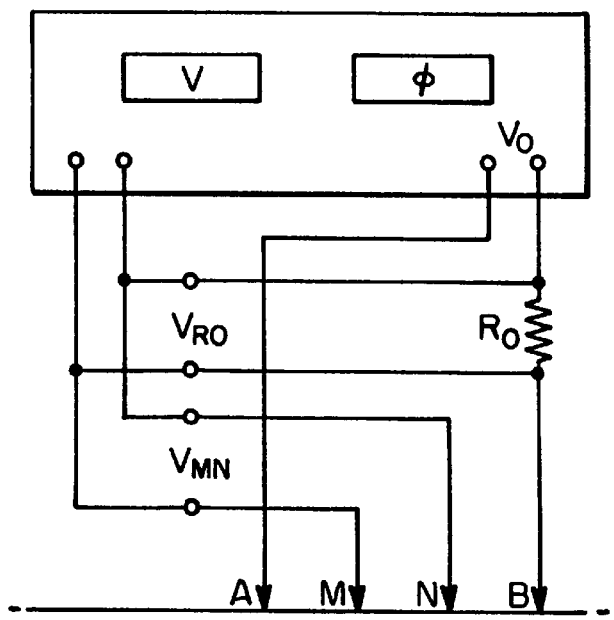
FIG_6

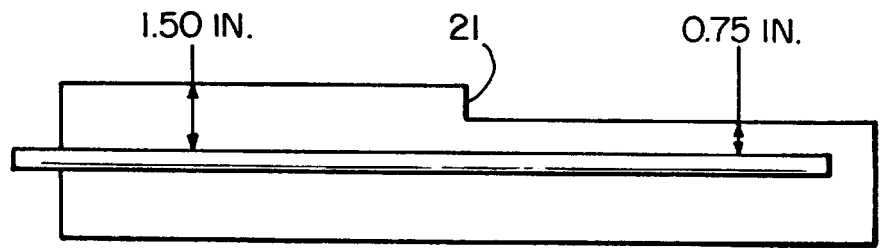
FIG_7A
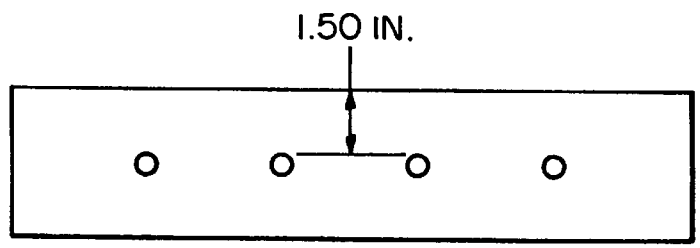
FIG_7B
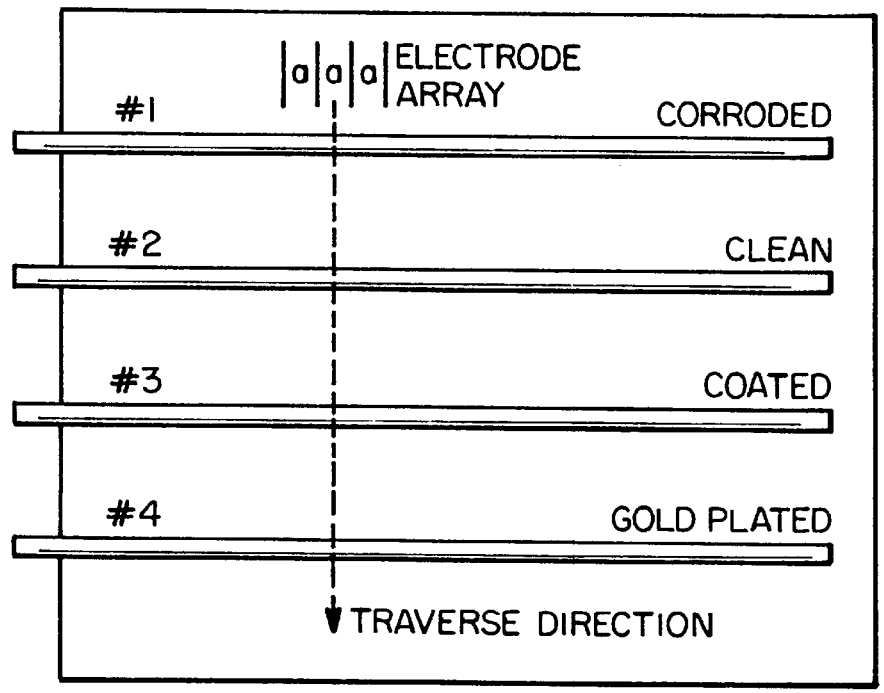
FIG_7C

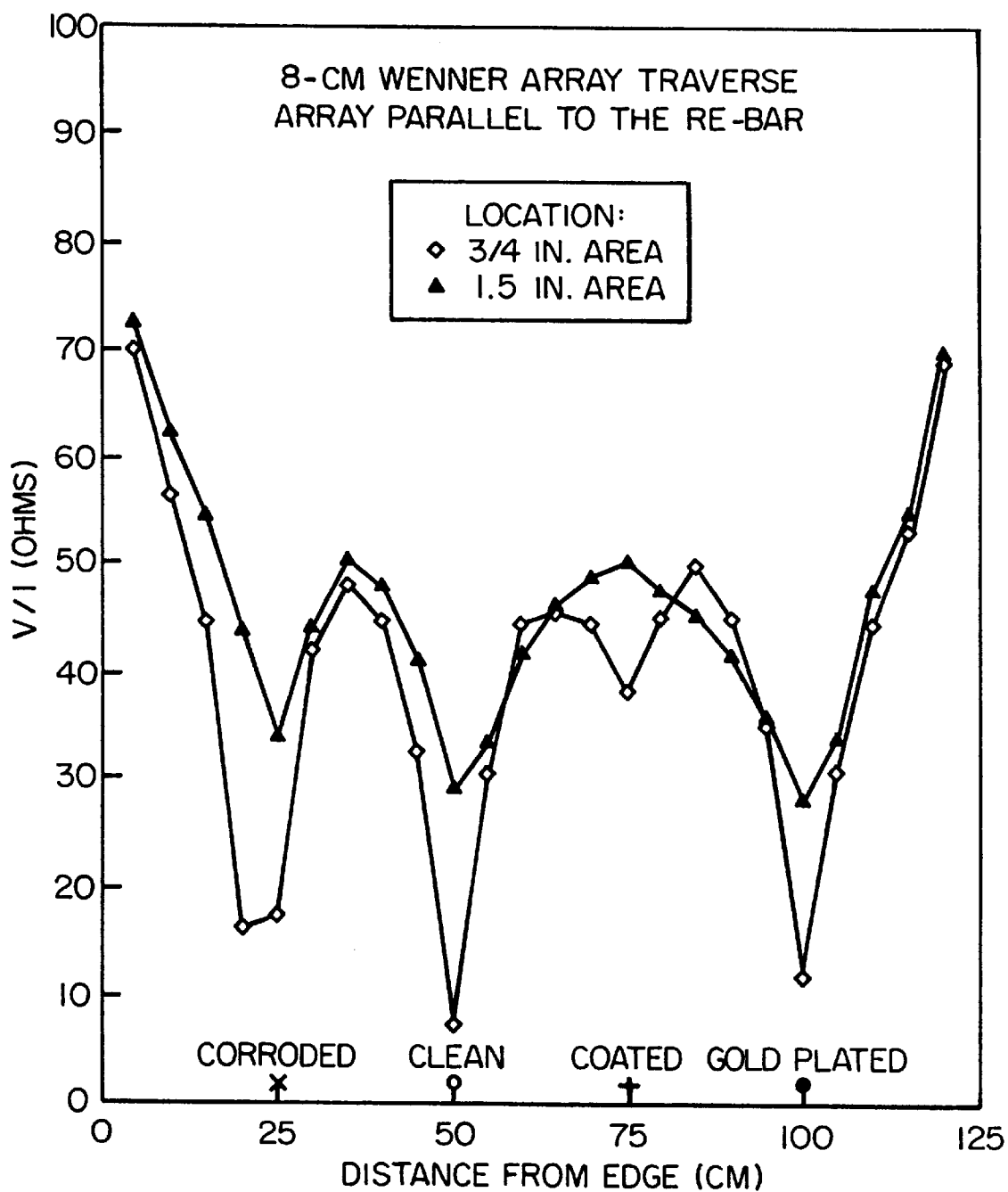
FIG_8

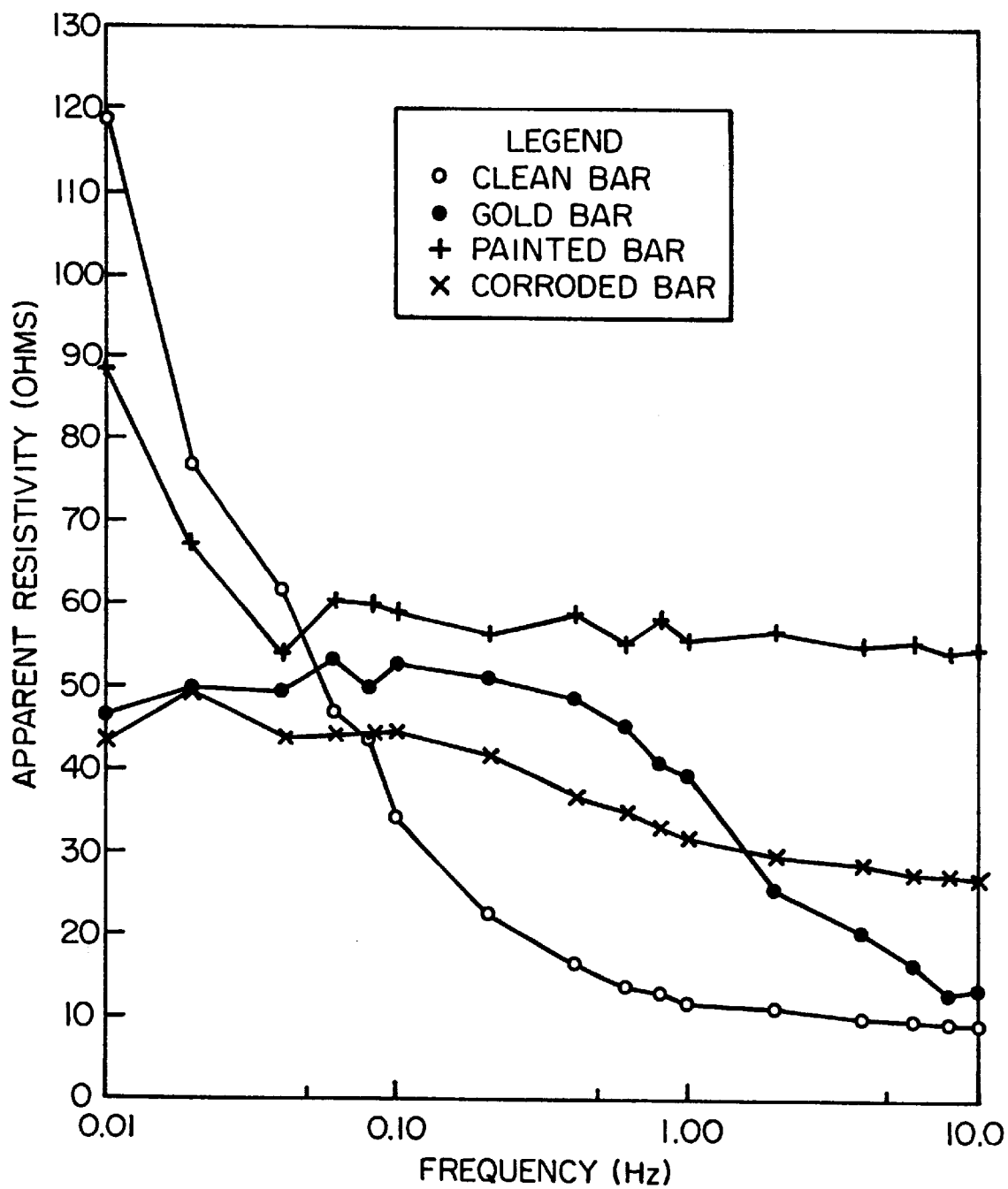
FIG_9

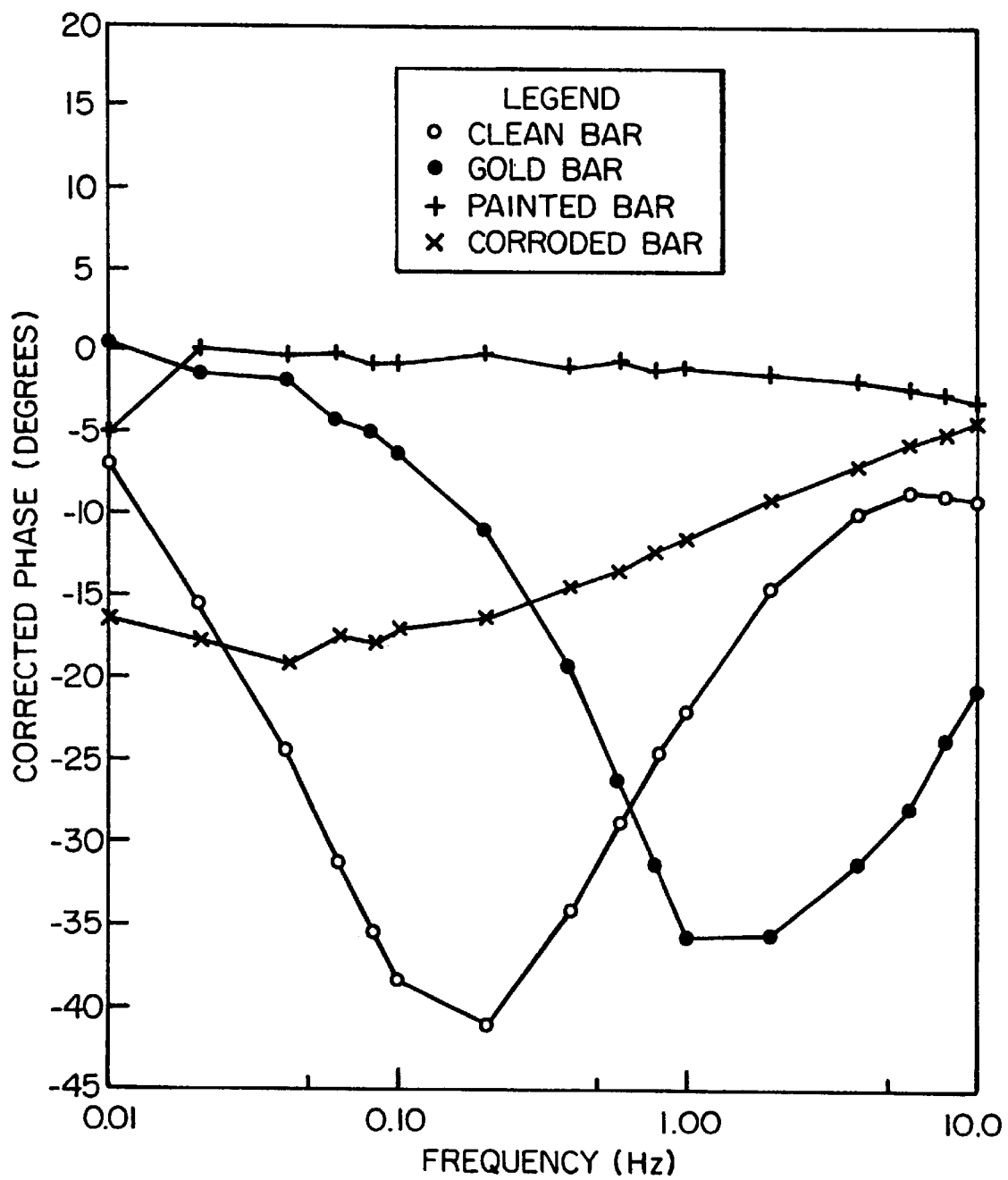
FIG_10

NON-DESTRUCTIVE METHOD OF DETERMINING THE POSITION AND CONDITION OF REINFORCING STEEL IN CONCRETE

BRIEF DESCRIPTION OF THE INVENTION

This invention relates to a non-destructive method of determining from the surface the position and condition of reinforcing steel in concrete.

BACKGROUND OF THE INVENTION

The existing reinforced concrete infrastructure (bridges, buildings, highways) in the U.S. and in many other countries is in bad condition due to cracking from the corrosion of the reinforcing bars. The early detection of the corrosion damage in reinforced concrete is quite challenging because the reinforcing bars are embedded in concrete; therefore, when the typical manifestations of corrosion distress become evident, stains on the concrete surface and cracking of the concrete structure, the reinforced concrete structure may be already seriously compromised.

The overriding cause of corrosion is the electrical potential between the metal and the solution. The rate of corrosion has been shown to be a very complex function of the metal solution interface, the reactive ions in the solution, the structure of the double layer, and the nature of reaction products which may form on the interface. The only direct measure of the state of the interface is the actual polarization voltage of the electrode formed at the interface with respect to a standard electrode. The measurement of this voltage forms the basis of several commercial systems designed to measure the corrosion potential and indirectly the corrosion rate. To make such a measurement, connection must be made to the reinforcing steel. This requires exposing the reinforcing steel which in itself is an operation which may lead to deterioration. Another approach to characterizing the metal solution interface which also requires connection to the reinforcing steel, is to determine impedance of the interface to current flow. If an alternating voltage is applied across a metal-solution interface current will flow and the voltage/current ratio is known as the Faradaic impedance. There is a relationship between the chemical state of the interface and the electrical impedance it offers to an impressed alternating current. The surface impedance, basically the resistance offered to the flow of current, is made up of two part, an energy absorbing or dissipative term which is called polarization resistance (Rp) and a capacitive component, $C_{d1}$. The double interface layer between steel and concrete is basically a charge separation which expands and contracts under an impressed electric field and behaves electrically as a capacitance. The polarization resistance is a measure of the energy absorbed in the oxidation or reduction reactions occurring at the surface and the double layer capacitance reflects the structure of the double layer itself. The quantitative relationship is complicated by the formation of passive layers, the role of chlorides in the surface reactions, and the role of oxygen. Several studies have established useful qualitative relationship between the electrical equivalent circuit elements Rp and $C_{d1}$ and the corrosion rate. Stearn and Geary, Stern, M. (1958) Corrosion, 14 pp 440, incorporated herein by reference, first showed the relationship between the polarization resistance Rp, and the corrosion rate. The result has been verified by many subsequent studies and the principle underlies a method of measuring the corrosion rate by contacting the rebar with one electrode and passing current to another electrode on the surface of the concrete.

For example, the rebar interface in well made concrete is coated with a passive layer or film of electrically insulating reaction products which presents a high polarization resistance and a capacitance dictated more by the thickness of the film than by the complex structure of the double layer adjacent to "bare" metal. During active corrosion this film is destroyed, the polarization resistance drops and the capacitance is set by the electrochemical properties of the interface. Further, the reaction or polarization resistance depends on frequency because the supply of ions to the surface is controlled by a diffusion law as well as by the mobility of the ions. Simple models of such diffusion controlled reactions show that the polarization resistance is frequency dependent and consequently complex. This frequency dependence is a function of the state of the interface, being quite different for the passive film or the active corrosion state.

In all of the processes responsible for corrosion there is an overriding requirement that the concrete must provide for relatively easy flow of ions, the electrical resistivity of the concrete must not be too high. Usually corrosion is initiated by carbonation which lowers the pH in the concrete or by the ingress of moisture, often accompanied by chlorides and permits ion dissolution to begin. Raising the moisture in the concrete also lowers it resistance so ion movement is facilitated and the corrosion rate increases.

A method to locate the reinforcing steel and measure the corrosion rate should have the following properties: It should from the surface, non-destructively, be able to locate the reinforcing steel and be able to localize the measurement so that portions of a steel undergoing corrosion can be distinguished from parts that are protected, measure the electrical resistivity of the concrete itself, and measure the properties of the interface, in particular the impedance because this is directly related to corrosion rate.

OBJECTS AND SUMMARY OF THE INVENTION

It is an object of this invention to provide a method of non-destructively locating reinforcing steel in concrete and determine the condition of selected portions.

It is another object of this invention to provide a method of locating reinforcing steel in concrete and its position by scanning an array of current and potential electrodes which contact the surface of the concrete.

It is a further object of this invention to provide a method of non-destructively estimating the corrosion rate of steel reinforcement in concrete.

The method for determining the position and condition of reinforcing steel in concrete comprises providing from the surface of the concrete an electrical current which flows through the concrete between spaced points on the surface, moving the spaced points to various positions and sensing the voltage generated by the current between two other spaced points on the surface for each position to determine the impedance of the structure between said other spaced points at said various positions, determining the position of minimum impedance to thereby locate the reinforcing steel and then determining from the impedance the condition of the reinforcing steel at the said position.

The foregoing and other objects of the invention will be more clearly understood from the following description when read in connection with the accompanying drawings, wherein:

FIG. 1 shows a four point electrode array in contact with the surface of concrete having an embedded reinforcing bar;

FIG. 2 shows the equivalent circuit of the impedance between the four points of the array;

FIG. 3 shows electrodes used to make contact with the surface of the concrete;

FIG. 4 is a pole—pole array of electrodes suitable for use in carrying on the present invention;

FIG. 5 shows a linear array of electrodes with different electrode spacing;

FIG. 6 shows a suitable instrument for use with the array of FIG. 1;

FIGS. 7A–C show a concrete test block with four spaced reinforcing bars of different composition used in illustrating the method of the present invention;

FIG. 8 shows the measured impedance obtained by scanning the test block with the reinforcing bars for bars ¾ and 1½ inches below the surface;

FIG. 9 shows the result of scanning the apparent resistivity of the rebars at 0.75 inches below the surface as a function of frequency.

FIG. 10 shows the phase angle of the rebars at 0.75 inches below the surface as a function of frequency.

DESCRIPTION OF PREFERRED EMBODIMENT

FIG. 1 shows a section of concrete 11 with an embedded reinforcing bar 12, having diameter "d" spaced a distance "D" from the upper surface 13. The resistivity of the concrete can be measured from the surface 13 using a four electrode array as shown in FIG. 1. The four electrodes supported by member 14 are labeled A, B, M and N. The electrodes are preferably non polarizing. A sketch of a suitable non-polarizing Cu—$CuSO_4$ electrodes is shown in FIG. 3. A saturated Cu—$CuSO_4$ solution is held in a sealed bottle 16 attached to a copper tube 17. The end of the tube is fitted with a sponge 18 which makes contact with the surface of the concrete. The fluid in the reservoir effectively is held by a partial vacuum preventing the flooding of the surface through the sponge. The use of a tough dense sponge material allows the array to be dragged across the surface with measurements made continuously.

Current is injected into the concrete from the surface 13 by applying a voltage between two electrodes A and B. The voltage drop produced by the resulting current flow in the concrete is measured between two other electrodes, M and N. This technique has been used in applied geophysics for over 70 years to measure the resistivity of the ground. The array shown, in which the electrode separation is "a", is called the Wenner array. There are many others, the Schlumberger, Dipole—Dipole, gradient, unipole, etc., each of which may present unique advantages if the purpose of the survey is to detect or map inhomogeneities in the medium. Such a surface array has been used to determine the resistivity of concrete and many studies have reported on the use of such a method for monitoring curing, assessing final quality, and detecting moisture ingress. There is no suggestion in the prior art of employing such an array to locate embedded reinforcing steel or of measuring the condition of the embedded reinforcing steel. We have discovered that if rebar is present in the concrete, the current path is distorted. Current is drawn into the rebar since it presents a low resistivity path. This decreases the voltage observed across the voltage electrodes MN. The effective penetration of the current, and hence the depth of detection of the rebar is determined by the ratio of a/D and the ratio of D/d. Small values of a/D sense only the concrete, and very large values of a/D are also insensitive to the presence of the rebar. The maximum response is achieved when $0.5 < a/D < 2$.

The equivalent circuit shown in FIG. 2 illustrates how the surface array is used for impedance measurements. This circuit is a schematic representation of the actual current path in FIG. 1. $Rc_1$, $Rc_2$ and $Rc_3$ are elements of the resistive path between the current electrode A and the rebar. Rr is the resistance in the rebar. $Z_1$ and $Z_2$ represents the surface impedance of the interface as the current enters and leaves the rebar, respectively. $Rc_4$ and $Rc_5$ are resistance paths between electrodes B and the rebar.

In the surface array the measurement is localized in the sense that only a relatively short portion of the rebar between the current electrodes actually participates in shorting the current. As in the direct contact method, the complete frequency response of the interface is recovered so that the corrosion state of the interface is measurable without the need to contact the rebar. While the schematic representation of FIG. 2 explains the form of the observed experimental data there is at present no way to covert the single circuit Z units into the true surface impedance. The voltage response vs. Frequency across MN is not the same as that across the impedance unit. This step has. to be carried out using a more realistic model with a full numerical solution for the voltage produced at M and N by a current injected at A and B as a function of depth and diameter of the rebar, surface impedance, concrete resistivity and frequency.

Measuring from the surface has a major advantage over other methods because the resistivity of the concrete $R_c$, can be determined either from data where a<<D, from a measurement away from the rebar or from an array which is not sensitive to the presence of the rebar such as occurs when the line on the surface is perpendicular to the rebar. In any event the concrete resistance (even if inhomogeneous) can be mapped from the surface and it becomes part of the model. The resistivity of the rebar is known (or as mentioned above may be set to zero) and so the parameters of inversion are the depth and effective diameter of the rebar and the desired surface impedance. The depth and diameter (effective conductance) of the rebar can in principle be determined using a standard geophysical inversion code which locates the conductor in an inhomogeneous medium. There will still be uncertainty about the diameter of a single rebar or "average" diameter of a group of reinforcing bars, but the diameter may be known from the original design specifications for the structure.

The apparatus that was designed and tested is shown in FIG. 1 and consists of an array of electrodes to be placed on the surface of a concrete structure. Two of the electrodes are for the purpose of injecting current and two others are required to measure a potential difference caused by the current made to flow in the concrete and its embedded reinforcement. The injected current is preferably alternating with a frequency range extending from $10^{-3}$ Hz to 100 kHz. The measurement is not limited to these frequencies and it may later be found useful to use dc excitation or to extend the frequencies upward into the $Mhz_k$ range.

The array shown, in FIGS. 1 and 5, the Wenner array, is only one of a variety of electrodes configurations which may be used. The most general array is one in which a rectangular grid is superimposed on the surface and a single current electrode A, with the return electrode B located are away, is placed successively at every nodal point of the grid, FIG. 4. Potentials at every point M are then measured relative to another distant reference electrode. From such data any electrode configuration can be constructed by suitable superposition of the single electrode results. Such an array is termed a pole—pole array. As a practical matter such a multiplicity of measurements might be time consuming, but one could certainly construct a large fixed array of electrodes (of the type described) which could then have current and voltage circuits switched to all combinations of the single electrode, pole—pole, responses. FIG. 5 shows an array of electrodes in which several different spacing can be achieved with the same apparatus. Simply swithcing between electrodes will allow "a" spacing of between 1 and 9 cm, more than enough to locate and characterize ½ inch (1.27 cm) rebar at depths up to 5 cm. Larger rebar, or multiple bars laced together can be detected deeper with larger "a" spacing.

The current injected is determined by the contact resistance of the current electrode and the source voltage, the actual concrete resistance being usually less than the contact resistance. We have observed contact resitance for the electrodes described below of 10 kohms to 100 kohms, so that for a voltage supply of up to 10V, the injected current will be fron $10^{-3}$ to $10^{-4}$ amps. In typical concrete the resistivity, p, can vary from 10 to $10^3$ ohm-m. So the resulting voltages for the Wenner array, $1p/2\pi a$ will range from 16 mV in the most conductive concrete to 160 mV in the most resistive (for a maximum spacing of 0.1 m). These ranges illustrate that there is more than adequate signal level to make very accurate measurements.

The instrumentation/circuit diagram for this configuration is shown in FIG. 6. A commercial digital synchronous detector was used. This unit provides a 10V output, Vo, at a desired frequency, which drives the current through the current electrodes A and B. The voltage, $V_{Ro}$, across the known series resistor Ro establishes the amplitude and phase of the current, Io, in the concrete. A second measurement of the voltage and its phase across electrodes M and N, $V_{MN}$ yield the complex impedance $Z=V_{MN}/I_{Ro}$ which for this Wenner array yields the complex apparent resistivity, $PA=2\pi a|Vmn|Io|e^{i\phi}$ where $\phi=$(phase of $I_o$–phase $V_{mn}$).

In carrying out the method of the present invention, the electrode array is scanned or positioned at various positions on the surface and the voltage across the sensing electrodes MN is observed or recorded. The reinforcing steel is located at the points of minimum voltage (impedance). The region of the reinforcing steel directly below the electrodes is being sensed and its impedance represents the condition of the steel. By moving the electrodes along the reinforcing steel, the condition of the steel at various locations can be determined. This is in contrast with the prior art methods where the corrosion can not be localized.

A test was designed to demostrate that proposed surface spectral resistivity method could locate the bars and distingusih between different surface impedances of the bars. To carry put the test a concrete block was cast. The block is shown in the side elevational and top views of FIGS. 7A, 7B and 7C respectively. Four 0.5 inch (12.7 mm) rods, #1, #2, #3 and #4 were held in place at the wooden forms on the ends of a mold, and by plastic ties attached to the crosspiece that served to step the thickness of the block at 21. Step 21 permitted the resistivity aray to sense rebar at 0.75 inch (19.05 mm) and 1.5 inch (38.1 mm) depths. The concrete mix proportions were: ASTM Type II cement 679 lb/yd$^3$ (403 kg/m$^3$), pozzolan 120 lb/yd$^3$ (71 kg/m$^3$), ater 325 lb/yd$^3$ (193 kg/m$^3$), ⅜" Pea Gravel 1025 lb/yd$^3$ (608 kg/m$^3$) top sand 1540 lb/yd$^3$ (914 kg/m$^3$), blend sand lb/yd$^3$.

The four embedded rebars were prepared as follows: #1 was a steel rebar corroded by exposing it to water for 24 hours, #2 was a steel rebar sandblasted clear a few hours before the casting, #3 was a copper bar spray-coated with an electrically insulating paint; and #4 was a steel rebar sandblasted, nickel electroplated and then gold electroplated. The gold plated bar was intended to represent a condition of complete chemical inertness in the rebar and the painted bar was intended to represent the condition of an almost perfect passive layer that should, in principle, offer only capacitive coupling to the concrete.

The small Wenner array shown in FIG. 1 with an 8.0 cm electrode separation was moved across the concrete block along a direction perpendicular to the rebar axis. The array was moved in increments of 5 cm and the voltage and current measurements were converted to apparent resistivity and plotted as a function of traverse distance in FIG. 8. Two such traverses were conducted, one over that portion of the block where the rebar was 0.75 inches (19.1 mm) below surface, the other where it was 1.5 inches (38 mm) below surface. The frequency of operation for this result was 1 Hz. The profiles clearly show the location of the corroded, clean and gold plated bars at 25, 50 and 100 cm respectively. As expected, the painted bar is well insulated from the concrete at this frequency (the capacitive coupling is apparently small), and only a small anomaly is seen when the bar is close to the surface (19.05 mm depth). Both apparent resistivity profiles increase near the edges of the bock because the current pattern is distorted by the air-concrete boundary. This is an edge effect for which there can be a correction if accurate values of concrete resistivity are needed near the edges of a structure.

This concrete is seen to be about 50 ohm meters between the rebar and the distortion introduced by the conductive rebars is about 50% when the rebar is buried 3 diameters (38.1 mm), with a very conservative assumption for the rate of falloff of the anomaly with depth. These results suggest that rebar should be easily detected at depths up to six times its diameter.

The variation of the apparent resistivity and the corrected phase of the voltage as a function of frequency is shown in FIGS. 9 and 10 respectively for the rebars at the 0.75 mm depth. All the bars show the anticipated decrease in apparent resistivity with increasing frequency, although the details of the response is quite different for each bar. The differences are even more distinct in the phase responses.

The painted bar appears to have a very small capacitive reactance for frequencies above 0.1 Hz since the phase shift is small for these frequencies and the resistivity is hardly perturbed by the presence of the bar. In other words no current is able to be shunted capacitively into the bar. The situation is much different for the other bars. The clear, gold and corroded bars appear to have well-developed phase peaks at 0.2 Hz, 1.0 Hz and 0.05 Hz respectively. These peaks clearly distinguish these three bars and in this sample would make it very simple to identify the bar from its spectral signature.

The new surface based method for measuring the frequency dependent complex impedance of a steel rebars embedded in concrete can be a powerful technique for the assessment of deteriorated concrete. The method, which uses an array of current and potential electrodes on the surface of the concrete can also measure the background resistivity of the concrete, can locate the rebar in the concrete, and can determine non linear properties of the response by varying the impressed currents by three orders of magnitude. It should be noted that the new method can provide a rapid estimate of corrosion rate from a simple non invasive measurement on the surface of a concrete structure.

What is claimed:

1. The method of determining the location of steel reinforcement in a concrete structure comprising the steps of:

applying voltage between two spaced points on the surface of the concrete to cause a current to flow along a path through said structure between the spaced points, measuring the voltage generated between two other spaced points by the flow of current, changing the path of said current and/or the position of said two other spaced points, and detecting the position where the voltage between said two other points decreases to a minimum to thereby determine the position of the steel reinforcement.

2. The method for determining the position and condition of reinforcing steel in concrete comprising:

providing from the surface of the concrete an electrical current which flows through the concrete between spaced points on the surface, moving the spaced points to various positions and sensing the voltage generated by the current between two other spaced points on the surface between said spaced points for each position to determine the impedance of the structure between said other spaced points at said various positions, and determining the position of minimum impedance to thereby locate the reinforcing steel and then determining from the impedance the condition of the reinforcing steel at the said position.

3. The method of determining from the surface the location of steel reinforcement in a concrete structure comprising the steps of:

applying an a-c voltage having a frequency selected between $10^{-3}$ Hz to 100 kHz between two spaced points on the surface of the concrete to cause an a-c current to flow along a path through said structure between the spaced points, measuring the a-c voltage generated between two other spaced points by the flow of the current, changing the path of said current and/or the position of said two other spaced points, and detecting the position where the voltage between said two other points decreases to a minimum to thereby determine the position of the steel reinforcement.

4. The method for determining from the surface the position and condition of reinforcing steel in concrete comprising:

providing from the surface of the concrete an a-c electrical current having a frequency greater than $10^{-3}$ Hz which flows through the concrete between spaced points on the surface, moving the spaced points to various positions and sensing the a-c voltage generated by the current between two other spaced points on the surface between said spaced points for each position between said two spaced points to determine the complex impedance of the structure between said other spaced points at said various positions, and determining the position of minimum impedance to thereby locate the reinforcing steel and then determining from the complex impedance the condition of the reinforcing steel at the said position.

5. The method of determining from the surface the condition of steel reinforcement in a concrete structure comprising the steps of:

applying an a-c voltage between two spaced points on the surface of the concrete to cause an a-c current to flow along a path through said steel reinforcement, measuring the amplitude and phase of the a-c current, measuring the amplitude and phase of the a-c voltage generated between two other spaced points by the flow of the a-c current, and determining from the amplitude and phase of the measured a-c current and a-c voltage the complex impedance between said spaced points to provide a measure of the condition of the steel reinforcement at said spaced points.

6. The method of claim 5 in which the frequency of the applied a-c voltage is greater than $10^{-3}$ Hz.

7. The method of claims 5 or 6 in which the two other spaced points are moved along the steel reinforcement to provide the complex impedance along the steel reinforcement.

8. The method for determining from the surface the position and condition of reinforcing steel in concrete comprising:

providing from the surface of the concrete an a-c electrical current which flows through the concrete between spaced points on the surface, measuring the amplitude and phase of the a-c electric current, moving the spaced points to various positions and sensing the amplitude and phase of the a-c voltage generated by the current between two other spaced points on the surface between said spaced points for each position between said two spaced points, determining from the amplitude and phase of said a-c electrical current and a-c voltage generator by the current the complex impedance between said two other spaced points, determining the position of minimum complex impedance to locate the reinforcing steel and then determining from the complex impedance the condition of the reinforcing steel at said position.

9. The method of claim 8 in which the frequency of the a-c electrical current is greater than $10^{-3}$ Hz.

10. The method of claims 8 or 9 in which the complex impedance along the reinforcing steel is determined by moving said other two spaced points along the reinforcing steel after it has been located.

* * * * *

UNITED STATES PATENT AND TRADEMARK OFFICE
CERTIFICATE OF CORRECTION

PATENT NO. : 5,855,721
DATED : January 5, 1999
INVENTOR(S) : Monteiro et al.

It is certified that error appears in the above-indentified patent and that said Letters Patent is hereby corrected as shown below:

```
On the title page, item [22]
```
   replace "Mar. 12, 1997" with --Mar. 11, 1997--.

Signed and Sealed this

Sixth Day of April, 1999

Attest:

Q. TODD DICKINSON

*Attesting Officer*    *Acting Commissioner of Patents and Trademarks*